United States Patent
Wathier et al.

(10) Patent No.: US 10,654,883 B2
(45) Date of Patent: May 19, 2020

(54) INORGANIC SALTS OF NICOTINIC ACID MONONUCLEOTIDE AS ANTI-AGING AGENTS

(71) Applicants: Jumpstart Fertility Pty Ltd, Coogee (AU); Life Biosciences, Inc., Boston, MA (US)

(72) Inventors: Michel Wathier, Allston, MA (US); Roland Dolle, Boston, MA (US); Sebastian Mario Marcuccio, Scoresby (AU); Rohan David Joyce, Scoresby (AU); Simon Tucker, Coogee (AU)

(73) Assignees: Jumpstart Fertility Pty Ltd, Coogee (AU); Life Biosciences, Inc., Boston, MA (US)

(*) Notice: Subject to any disclaimer, the term of this patent is extended or adjusted under 35 U.S.C. 154(b) by 0 days.

(21) Appl. No.: 16/374,461

(22) Filed: Apr. 3, 2019

(65) Prior Publication Data
US 2019/0352325 A1    Nov. 21, 2019

Related U.S. Application Data

(63) Continuation of application No. PCT/US2019/022555, filed on Mar. 15, 2019.
(60) Provisional application No. 62/671,807, filed on May 15, 2018.

(51) Int. Cl.
| | | |
|---|---|---|
| A01N 43/04 | (2006.01) | |
| A61K 31/70 | (2006.01) | |
| C07H 19/048 | (2006.01) | |
| A61P 15/08 | (2006.01) | |

(52) U.S. Cl.
CPC ............ *C07H 19/048* (2013.01); *A61P 15/08* (2018.01)

(58) Field of Classification Search
None
See application file for complete search history.

(56) References Cited

U.S. PATENT DOCUMENTS

| | | | |
|---|---|---|---|
| 3,700,654 A | 10/1972 | Brusca | |
| 5,654,286 A * | 8/1997 | Hostetler | A61K 9/06 514/47 |
| 9,855,289 B2 | 1/2018 | Normington et al. | |
| 9,919,003 B2 | 3/2018 | Normington et al. | |
| 2003/0095959 A1 * | 5/2003 | Mayne | A61K 8/35 424/94.4 |
| 2016/0272668 A1 * | 9/2016 | Dellinger | C07H 19/048 |
| 2016/0279161 A1 | 9/2016 | Wu et al. | |
| 2018/0147227 A1 | 5/2018 | Normington et al. | |
| 2018/0163243 A1 | 6/2018 | Wu et al. | |
| 2018/0282362 A1 | 10/2018 | Carr et al. | |

FOREIGN PATENT DOCUMENTS

| | | |
|---|---|---|
| GB | 1561954 A | 3/1980 |
| WO | WO2016198948 A1 | 12/2016 |
| WO | WO2017024255 A1 | 2/2017 |
| WO | WO2017059249 A1 | 4/2017 |

OTHER PUBLICATIONS

Semin et al. (2003). Salt Screening and Selection. Burger's Medicinal Chemistry and Drug Discovery, 381-400.*
Fini et al. International Journal of Pharmaceutics (1999), vol. 187, pp. 163-173.*
International Search Report and Written Opinion dated May 13, 2019 for PCT Application No. PCT/US2019/022555, filed Mar. 15, 2019.
Trammell, S. A., et al. "Nicotinamide riboside is uniquely and orally bioavailable in mice and humans", Nat Commun. Oct. 10, 2016;7(1): 1-14.

* cited by examiner

*Primary Examiner* — Patrick T Lewis
(74) *Attorney, Agent, or Firm* — Cooley LLP

(57) ABSTRACT

The present invention relates to inorganic salts of nicotinic acid mononucleotides and compositions of Formula I, useful in the treatment of disorders and diseases associated with deficiencies in $NAD^+$:

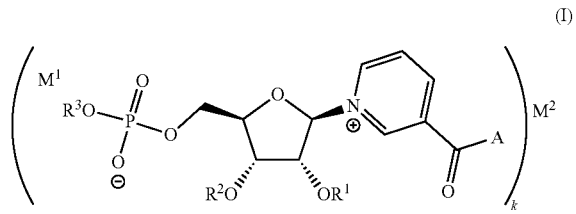

wherein A, $M^1$, $M^2$, k, $R^1$, $R^2$, and $R^3$ are as described herein.

6 Claims, 2 Drawing Sheets

FIGURE 1

| Catalogue No. | External Temp (°C) | % Degradation (Weeks) | | | | | | | | | |
|---|---|---|---|---|---|---|---|---|---|---|---|
| | | 1 | 2 | 3 | 4 | 5 | 6 | 7 | 8 | 9 | 10 |
| NAMN | 25 | 1 % | 2 % | 3 % | 3.8 % | 6.5 % | 8.3 % | 9.1 % | 10.7 % | - | 12.3 % |
| | 40 | 3.8 % | 15.3 % | | | | | | | | |
| | 60 | 35 %* | - | - | - | - | - | | | | |

Aqueous solution conditions: 5-8 mg fully dissolved in D$_2$O

FIGURE 2

| Catalogue No. | External Temp (°C) | % Degradation (Weeks) | | | | | | | | | | |
|---|---|---|---|---|---|---|---|---|---|---|---|---|
| | | 5 | 6 | 7 | 8-22 | 24 | 26 | 28 | 30 | 32 | 34 | 38 |
| I-001 | 25 | 1% | 1% | 2% | ------ | 3.8% | 3.8% | 4.3% | 4.3% | 4.3% | 4.3% | 4.3% |
| I-002 | 25 | 1% | 1% | 1% | ------ | 4.7% | 4.8% | 4.8% | 4.8% | 4.8% | 4.8% | 4.8% |
| I-003 | 25 | 1% | 1% | 1% | ------ | 2.6% | 2.9% | 2.9% | 3.2% | - | 4.9% | |
| I-004 | 25 | 1% | 1% | 1% | ------ | 1.9% | 1.9% | 2.1% | 2.1% | - | 2.6% | |

Integrals are kept consistent between NMR's but percentage error may be ~2%

INORGANIC SALTS OF NICOTINIC ACID MONONUCLEOTIDE AS ANTI-AGING AGENTS

RELATED APPLICATIONS

This application is a continuation application of International Application No.: PCT/US2019/022555, filed on Mar. 15, 2019, which claims priority to, and the benefit of, U.S. Provisional Application No. 62/671,807, filed on May 15, 2018, the contents of which are incorporated herein by reference in their entireties.

FIELD OF THE DISCLOSURE

The present invention relates to inorganic salts of nicotinic acid mononucleotides and compositions thereof useful in the treatment of disorders and diseases associated with aging.

BACKGROUND OF THE DISCLOSURE

Aging is the result of complex interactions involving biological, physical, and biochemical processes that cause dysfunctions in cells and organs which manifests in a variety of diseases and other outcomes. For example, female fecundity is markedly sensitive to the effects of ageing. For example, the USA Centers for Disease Control has reported that the percentage of assisted reproductive technology (ART) associated pregnancies and births percentages declined steadily among women in their mid-30s onward from approximately 25% of ART cycles resulting in singleton live births to 14% by the age of 40 (Centers for Disease Control and Prevention, American Society for Reproductive Medicine, Society for Assisted Reproductive Technology. 2011 Assisted Reproductive Technology National Summary Report. Atlanta (Ga.): US Dept of Health and Human Services; 2013). This trend is markedly increased above the age of 40 with the CDC reporting that women older than age 44 have a very low likelihood of success. The percentages of live births and singleton live births declined to about 1% in this group. It is generally considered that a woman's age is the most important factor affecting the chance of a live birth when her own eggs (oocytes) are used.

It is understood that the qualitative deterioration of oocytes due to aging is a fundamental factor in the decline in fertility. In older women, for example, the oocytes are reported to be susceptible to abnormal chromosome division, exhibit decreased mitochondrial quality, low ATP production, increased oxidative stress, and decreased antioxidant levels (Nelson S M, Telfer E E, Anderson R A. The ageing ovary and uterus: new biological insights. Hum Reprod Update. 2013; 19:67-83.; Wilding M. Potential long-term risks associated with maternal aging (the role of the mitochondria). Fertil Steril. 2015; 103:1397-401; 3. Meldrum D R, Casper R F, Diez-Juan A, Simon C, Domar A D, Frydman R. Aging and the environment affect gamete and embryo potential: can we intervene? Fertil Steril. 2016; 105:548-59).

For all of the foregoing reasons, the oocyte represents an excellent target tissue for the evaluation of therapeutic modalities that are expected to have an impact upon the ageing process and, furthermore, offer the prospect of addressing age-related infertility.

One such possible therapeutic modality for treating ageing comprises agents which boost therapeutic levels of $NAD^+$. $NAD^+$ is an essential component of cellular processes necessary to support various metabolic functions. The classic role of $NAD^+$ is a co-enzyme that catalyzes cellular redox reactions, becoming reduced to NADH, in many fundamental metabolic processes, such as glycolysis, fatty acid beta oxidation, or the tricarboxylic acid cycle. In addition to playing these roles, $NAD^+$ has a critical role as the substrate of $NAD^+$-consuming enzymes such as poly-ADP-ribose polymerases (PARPs), sirtuins, and CD38/157 ectoenzymes. These $NAD^+$-consuming enzymes have been known to mediate many fundamental cellular processes.

There are five major precursors and intermediates to synthesize $NAD^+$: tryptophan, nicotinamide, nicotinic acid (NA), nicotinamide riboside (NR), and nicotinamide mononucleotide (NMN). $NAD^+$ can be synthesized de novo by the conversion of the amino acid tryptophan through multiple enzymatic steps to nicotinic acid mononucleotide (NaMN). NaMN is converted to nicotinic acid dinucleotide ($NaAD^+$) by NMN/NaMN adenylyltransferases (NMNATs) and then amidated to $NAD^+$ by $NAD^+$ synthetase.

In mammals, a major pathway of $NAD^+$ biosynthesis is the salvage pathway from nicotinamide. Nicotinamide is converted to NMN, a key $NAD^+$ intermediate, by nicotinamide phosphoribosyltransferase (NAMPT), the rate-limiting enzyme in this pathway. NMNATs then convert NMN into $NAD^+$. NAMPT plays a critical role in regulating cellular NAD+levels. On the other hand, nicotinic acid is converted to NaMN by nicotinic acid phosphoribosyltransferase (NPT). NR needs to be converted to NMN by nicotinamide ribose kinases, NMRK1 and NMRK2 (also known as NRK1 and NRK2), which phosphorylate NR 16. Maintenance of adequate $NAD^+$ biosynthesis is paramount for cell survival and function. Derailment from normal $NAD^+$ homeostasis substantially affects not only the $NAD^+$/NADH pool required for redox reactions but also activities of $NAD^+$-dependent enzymes for crucial cellular functions.

It is now becoming a consensus that $NAD^+$ levels decline at cellular, tissue/organ, and organismal levels during the course of aging. Activities of $NAD^+$-consuming enzymes are affected by this $NAD^+$ decline, contributing to a broad range of age-associated pathophysiologies Nicotinamide adenine dinucleotide is an enzyme co-factor that is essential for the function of several enzymes related to reduction-oxidation reactions and energy metabolism. (Katrina L. Bogan & Charles Brenner, *Nicotinic Acid, Nicotinamide and Nicotinamide Riboside: A Molecular Evaluation of $NAD^+$ Precursor Vitamins in Nutritions.* 28, Annual Review of Nutrition 115 (2008)). $NAD^+$ functions as an electron carrier in energy metabolism of amino acids, fatty acids and carbohydrates (Bogan & Brenner, Annu. Rev. Nutr. 2008, 28, 115-130). $NAD^+$ is critical for redox reactions and as a substrate for signaling by the PARPs (poly adenoside diphophosphate-ribose polymerases) and the sirtuins (SIRTI to SIRT7), in the regulation of DNA repair, energy metabolism, cell survival and circadian rhythms which have all been shown to be critical in the ageing process (Bronkowski, M. S. & Sinclair, D., *Nat. Rev. Mole. Cell. Bio.*, 17, 679-690, (2016)). Raising $NAD^+$ concentrations delays aging in yeast, files and mice (Mouchiroud et al. *Cell* 154, 464-471, (2014)). It has recently also been demonstrated that $NAD^+$ directly regulates protein-protein interactions, the modulation of which may protect against cancer and radiation exposure as well as having a direct impact on aging (Li et al., Science 355, 1312-1317, 2017). Thus increasing bodies of evidence support the idea that interventions using $NAD^+$ intermediates, such as NMN and NR, can bolster the system by restoring the available $NAD^+$ and mitigate physiological decline associated with aging.

Although NAD⁺ can be synthesized de novo from the amino acid tryptophan, this process does not occur in all tissues, requiring most cells to rely on the salvage pathway (described above) for regenerating NAD⁺ from other intracellular intermediates, which are primarily made available through dietary sources (Christopher R. Martens, et al., *Nat. Commun.* 9, 1286, (2018) and Bogan, K. L. & Brenner, C., *Annu. Rev. Nutr.* 28, 115-130, (2008)). Other NAD precursors like nicotinic acid and nicotinamide can also be administered to boost NAD cellular bioavailability. However, clinically relevant levels of nicotinic acid are associated with undesirable flushing at therapeutic doses (MacKay, D., Hathcock, J. & Guarneri, E., *Nutr. Rev.* 70, 357-366 (2012)). and nicotinamide does not reliably activate (and may even inhibit) sirtuins despite raising concentrations of NAD (Bitterman, K. J., et al., *J. Biol. Chem.* 277, 45099-45107 (2002); Guan, X., et al., *PLoS One.* 9, e107729 (2014); and Trammell, S. A. et al. *Nat. Commun.* 7, 12948 (2016)). Therefore, administration of nicotinic acid or nicotinamide is unlikely to be widely adopted for maintaining health and function with aging.

In contrast to nicotinic acid and nicotinamide, administration of NAD⁺ metabolites such as nicotinamide mononucleotide (NMN) or nicotinamide riboside (NR), appears to increase levels of NAD⁺ and improves multiple physiological functions in animal models (Yoshino, J. et al., *Cell Metab.* 14, 528-536 (2011); Mills, K. F. et al., *Cell Metab.* 24, 795-806 (2016); and Frederick, D. W. et al., *Cell Metab.* 24, 269-282 (2016)). At least one of these metabolites has been reported to be well tolerated in humans leading to elevation of NAD levels and improved physiological functions albeit that further studies are required to confirm the findings of this exploratory study (Christopher R. Martens, et al., *Nat. Commun.* 9. 1286, (2018)). Furthermore, a recent study showed that single doses of NR stimulated blood cellular NAD⁺ metabolism in healthy humans in a dose-dependent manner (Trammell, S. A. et al., *Nat. Commun.* 7, 12948 (2016)), showing the limitation of this metabolite. However, many of the known NAD⁺ metabolites are unstable in a variety of physiological environments and thus do not lend themselves to viable pharmaceutical drugs for administration to patients in need of such metabolites for boosting the NAD⁺ levels in said patients.

Given the central role that NAD⁺ plays in critical cellular and physiological pathways, developing novel stable agents with improved properties that can elevate NAD⁺ levels in disease states and/or during the aging process is necessary to improve the human condition.

SUMMARY OF THE DISCLOSURE

Provided herein are inorganic salts of NaMN which salts surprisingly increase cellular NAD⁺ levels to a greater extent than NaMN, and which exhibit greater chemical stability than NaMN.

A first aspect of the present disclosure relates to salts of Formula (I):

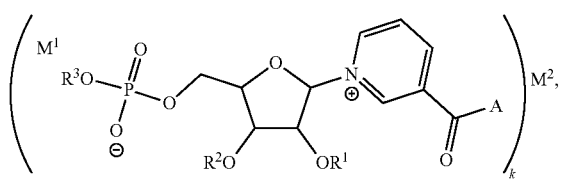

and enantiomers, stereoisomers, and tautomers thereof, wherein
A is O⁻;
$M^1$ and $M^2$ are independently an inorganic cation;
$R^1$ and $R^2$ are independently H, $C_1$-$C_6$alkyl, $C_1$-$C_6$haloalkyl, ($C_0$-$C_3$alkylene)C(O)$C_1$-$C_6$alkyl, —C(O)OR$^a$, —C(O)NR$^a$R$^b$, or —[CH$_2$—CH$_2$—O]$_n$—R$^a$,
or $R^1$ and $R^2$, taken together with the atom to which each is attached, form a 5-membered heterocyclic ring optionally substituted with one or more substituents selected from $C_1$-$C_6$alkyl, $C_2$-$C_6$alkenyl, $C_2$-$C_6$alkynyl, ($C_0$-$C_3$alkylene)$C_3$-$C_8$cycloakyl, ($C_0$-$C_3$alkylene)heterocycloakyl, ($C_0$-$C_3$alkylene)$C_6$-$C_{14}$aryl, or ($C_0$-$C_3$alkylene)heteroaryl;
$R^3$ is a negative charge, H, or $C_1$-$C_6$ alkyl;
$R^a$ and $R^b$ are independently, at each occurrence, H, or $C_1$-$C_6$alkyl, wherein the alkyl is optionally substituted with one or more substituents selected from ($C_0$-$C_3$alkylene)$C_3$-$C_8$cycloakyl, ($C_0$-$C_3$alkylene)heterocycloakyl, ($C_0$-$C_3$alkylene)$C_6$-$C_{14}$aryl, and ($C_0$-$C_3$alkylene)heteroaryl;
k is 1 or 2; and
n is an integer from 1 to 8;
provided that when $R^3$ is H or $C_1$-$C_6$alkyl then $M^1$ is absent.

Another aspect of the present disclosure relates to a pharmaceutical composition comprising a salt of Formula Ia, or a pharmaceutically acceptable salt thereof, in association with a pharmaceutically acceptable carrier.

Another aspect of the present disclosure relates to a method of treating or preventing an age-related infertility comprising administering to a subject in need thereof, an effective amount of a salt of Formula (I), or enantiomer, stereoisomer, or tautomer thereof.

Another aspect of the present disclosure relates to a method of treating or preventing infertility comprising administering to a subject in need thereof, an effective amount of a salt of Formula (I), or enantiomer, stereoisomer, or tautomer thereof.

Another aspect of the present disclosure relates to a salt of Formula (I), or enantiomer, stereoisomer, or tautomer thereof, for use in the manufacture of a medicament for treating age related infertility.

Another aspect of the present disclosure relates to a salt of Formula (I), or enantiomer, stereoisomer, or tautomer thereof, for use in the manufacture of a medicament for use in treating infertility.

In another aspect, the present invention relates to a method of treating or preventing an age-related disorder, comprising administering to a subject in need thereof, a therapeutically effective amount of a pharmaceutical composition of the salt of Formula I.

Another aspect of the present disclosure relates to a method of improving oocyte quality and maturation, comprising administering to a subject in need thereof, a therapeutically effective amount of a salt of Formula I.

Another aspect of the present disclosure relates to the use of a salt of Formula (I), or enantiomer, stereoisomer, or tautomer thereof, in the manufacture of a medicament for treating an age-related disorder.

In another aspect, the invention comprises treatment of an oocyte with a salt of Formula (I) ex vivo prior to implantation into a subject, for the treatment of age-related infertility.

In another aspect, the invention comprises treatment of a blastocyst with a salt of Formula (I) ex vivo prior to implantation into a subject, for the treatment of age-related infertility.

In another aspect, the invention comprises treatment of an oocyte with a salt of Formula (I) ex vivo prior to implantation into a subject, for the treatment of infertility.

In another aspect, the invention comprises treatment of a blastocyst with a salt of Formula (I) ex vivo prior to implantation into a subject, for the treatment of infertility.

In another aspect, a salt of Formula (I) is provided as a component in solution for use in treating a cell ex vivo for use in the treatment of an age related disorder. In some embodiments, the age related disorder is age-related infertility. In other aspects a salt of Formula (I) is provided as a component in solution for use in treating a cell ex vivo for use in the treatment of infertility.

Another aspect of present disclosure relates to a process for preparing salts of Formula (I), comprising contacting a nicotinic acid mononucleotide derivative of Formula II with a metal-alkali hydroxide under suitable conditions effective to produce the salt of Formula I.

The present disclosure also relates to methods of accelerating recovery from a disease or disorder. The method comprises administering to a subject in need thereof an effective amount of a salt of Formula (I) in combination with the prescribed treatment of said disease.

In another aspect, the present disclosure relates to a cell culture medium for in vitro fertilization comprising: one or more salts of Formula (I) and culturing agents.

BRIEF DESCRIPTION OF THE FIGURES

FIG. 1 is a table representing stability tests of control compounds NaMN in aqueous solution at various time periods.

FIG. 2 is a table representing stability test of salts I-001, I-002, I-003, and I-004 in aqueous solution at various time periods.

DETAILED DESCRIPTION OF THE DISCLOSURE

The present disclosure relates to salts of Formula (I) and compositions comprising the same, that are useful in treating or preventing an age-related disorder such as age related infertility amongst other such disorders. The methods of the present disclosure can be used in the treatment of a variety of diseases and disorders by preventing or ameliorating anti-aging processes and aiding cellular restoration processes.

Salts of Formula (I) are potent and are efficacious at clinically achievable doses; are stable in a variety of potential dosage forms; possess acceptable solubility, acceptable pH, are crystalline, have a reduced propensity to absorb water, display ease of handling, —all of which are consistent with the development, manufacture and use of a medicament. In addition, the salts disclosed herein offer increased biological activity toward increased cellular NAD+ levels, increased stability and more physiologically acceptable pH.

Enhanced Stability

The salts of Formula (I) display a significantly slow rate of degradation. For example, the salts of Formula (I) do not show signs of degradation after 36 weeks at room temperature (20-22° C.) and/or under suitable storage conditions. The salts of Formula (I) display stronger stability and longer shelf life and/or storage life than both neutral nicotinic acid mononucleotide. Thus, in some embodiments, the salt has enhanced solid form stability. Yet in another embodiment, the salts of the instant disclosure show greater stability than NaMN.

The salts of Formula (I) also show increased stability in aqueous solution. In some embodiments, no significant degradation of the salts of Formula (I) in aqueous solution phase occurs for up to 38 weeks. In other embodiments, degradation of the salts of Formula (I) is less than 5% after 38 weeks in an aqueous solution. The salts of Formula (I) remain stable in aqueous solution after 7 weeks with 1% degradation or less. In further embodiments, the salts of the disclosure remain stable in solutions after 30 weeks with 2.5% degradation or less. The In one embodiment, the salts of Formula (I) are also more stable in aqueous solution than their neutral nicotinic acid mononucleotide or nicotinic acid riboside counterparts. This, in some embodiments, the salt has enhanced aqueous solubility.

The salts of Formula (I) are also stable under physiological conditions. In solution, the salts of Formula (I) are closer to physiological pH than their nicotinic acid mononucleotide or nicotinic acid riboside counterparts. In some embodiments, the salts of the instant disclosure are less acidic and closer to physiological pH than NaMN. In some embodiments, the salt of Formula (I), in solution at relevant concentrations, is between pH 6.0-7.5. In some embodiments, the salt of Formula (I), in solution at relevant concentrations, is between pH 6.2-7.3. In some embodiments, the salt of Formula (I), in solution at relevant concentrations, is between pH 6.5-7.0. In some embodiments, the salt of Formula (I), in solution at relevant concentrations, is between pH 6.7-6.8. Stability under physiological conditions of the salts of Formula (I) offers a significant biological activity advantage for cell rejuvenation over their neutral nicotinic acid mononucleotide or nicotinic acid riboside counterparts. The salts of Formula (I) are also more soluble in aqueous solution than their neutral nicotinic acid mononucleotide or nicotinic acid riboside counterparts.

In one aspect of disclosure relates to a salt of Formula I

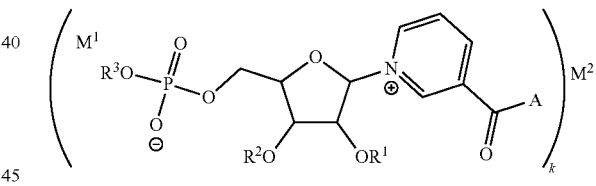

wherein A, $M^1$, $M^2$, $R^1$, $R^2$, and $R^3$ are as described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatomns). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—(C$_1$-C$_6$) alkyl, (C$_1$-C$_6$) alkyl, C$_1$-C$_6$ alkoxy, (C$_1$-C$_6$)haloalkyl, C$_1$-C$_6$ haloalkoxy, —O—(C$_2$-C$_6$) alkenyl, —O—(C$_2$-C$_6$) alkynyl, (C$_2$-C$_6$) alkenyl, (C$_2$-C$_6$) alkynyl, —OH, —OP(O)(OH)$_2$, —OC(O)(C$_1$-C$_6$) alkyl, —C(O)C$_1$-C$_6$)alkyl, —OC(O)O(C$_1$-C$_6$) alkyl, —NH$_2$, —NH((C$_1$-C$_6$) alkyl), —N((C$_1$-C$_6$) alkyl)$_2$, —NHC(OX)C$_1$-C$_6$) alkyl, —C(O)NH(C$_1$-C$_6$) alkyl, —S(O)$_2$(C$_1$-C$_6$) alkyl, —S(O)NH(C$_1$-C$_6$) alkyl, and S(O)N((C$_1$-C$_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—(C$_1$-C$_6$) alkyl, (C$_1$-C$_6$) alkyl, —O—(C$_2$-C$_6$) alkenyl, —O—(C$_2$-C$_6$) alkynyl, (C$_2$-C$_6$) alkenyl, (C$_2$-C$_6$) alkynyl, —OH, —OP(O)(OH)$_2$, —OC(O)(C$_1$-C$_6$) alkyl, —C(O)(C$_1$-C$_6$) alkyl, —OC(O)O(C$_1$-C$_6$) alkyl, NH$_2$, NH((C$_1$-C$_6$) alkyl), N((C$_1$-C$_6$) alkyl)$_2$, —S(O)$_2$—(C$_1$-C$_6$) alkyl, —S(O)NH(C$_1$-C$_6$) alkyl, and S(O)N((C$_1$-C$_6$) alkyl)$_2$. The substituents can themselves be optionally substituted. Furthermore when containing two fused rings the aryl groups herein defined may have a saturated or partially saturated ring fused with a fully aromaticring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 24 ring atoms, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d] thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have asaturated or partially saturated ring fused with a fully aromaticring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a (C$_1$-C$_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a C$_1$-C$_6$ alkylene. An alkylene may further be a C$_1$-C$_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Cycloalkyl" means monocyclic or polycyclic saturated carbon rings (e.g., fused, bridged, or spiro rings) containing 3-18 carbon atoms (e.g., C$_3$-C$_{10}$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Heterocyclyl" or "heterocycloalkyl" means monocyclic or polycyclic rings (e.g., fused, bridged, or spiro rings) containing carbon and heteroatoms taken from oxygen, nitrogen, or sulfur and wherein there is not delocalized $\pi$ electrons (aromaticity) shared among the ring carbon or heteroatoms. The heterocycloalkyl can be a 3-, 4-, 5-, 6-, 7-, 8-, 9-10-, 11-, or 12-membered ring. The heterocycloalkyl ring structure may be substituted by one or more substituents. The substituents can themselves be optionally substituted. Examples of heterocyclyl rings include, but are not limited to, oxetanyl, azetadinyl, tetrahydrofiuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl. In accordance with the present disclosure, 3- to 10-membered heterocyclyl refers to saturated or partially saturated non aromatic rings structures containing between 3 and 10 atoms in which there is at least one heteroatoms selected from the group N, O, or S.

The term "hydroxyalkyl" means an alkyl group as defined above, where the alkyl group is substituted with one or more —OH groups. Examples of hydroxyalkyl groups include HO—CH$_2$—, HO—CH$_2$—CH$_2$— and CH$_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—NH$_2$, R≠H), secondary (R$_2$—NH, R$_2$≠H) and tertiary (R$_3$—N, R≠H) amines. A substituted amine is intended to mean an amine where at least one of the hydrogen atoms has been replaced by the substituent.

The term "amino" as used herein means a substituent containing at least one nitrogen atom. Specifically, NH$_2$, —NH(alkyl) or alkylamino, —N(alkyl)$_2$ or dialkylamino, amide-, carbamide-, urea, and sulfamide substituents are included in the term "amino".

The term "oxo" as used herein refers to an "=O" group.

The term "isomer" refers to salts and/or compounds that have the same composition and molecular weight but differ in physical and/or chemical properties. The structural difference may be in constitution (geometric isomers) or in the ability to rotate the plane of polarized light (stereoisomers). With regard to stereoisomers, the salts of Formula (I) may have one or more asymmetric carbon atom and may occur as racemates, racemic mixtures and as individual enantiomers or diastereomers.

The term "cation" contemplates all organic and inorganic positively charged ions. The cation in the compounds of formula (I) may include, but are not limited to, those described in "Handbook of Pharmaceutical Salts: Properties, Selections and Use", Stahl, H. and Wermuth, C., ed., Verlag Helvetica Chemica Acta, Zurich, Wiley-VCH, 2002.

The term "inorganic cation" refers to any positively charged inorganic atom or group of atoms. Exemplary inorganic cations are the alkali metals, (e.g., lithium, sodium, and potassium), the alkaline earth metals (e.g., calcium and magnesium), manganic, ferrous, cobalt, thallium, manganous, and ammonium (NH$_4^+$).

The term "degrade," as used herein, means to chemically decompose. Degradation is distinct from melting in that it involves the breaking of chemical bonds or the formation of new chemical bonds. Methods of degradation can include hydrolysis, solventolysis, thermolysis, or oxidation.

The disclosure also includes pharmaceutical compositions comprising an effective amount of a disclosed salt and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a salt or pharmaceutical composition is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying causes of symptoms, inhibiting the disorder or disease, e.g., arresting the development of the disorder or disease, relieving the disorder or disease, causing regression of the disorder or disease, relieving a condition caused by the disease or disorder, or stopping or alleviating the symptoms of the disease or disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed salt or a composition to a subject, or administering a prodrug derivative or analog of the salt or composition to the subject, which can form an equivalent amount of active salt within the subject's body.

The term "oocyte" is synonymous with the term "egg" and is used in this disclosure to mean a female mammalian gametocyte or germ cell.

The term "zygote" is used in this disclosure to mean a fertilized egg or adiploid cell formed from the fusion of an oocyte and sperm during fertilization.

The term "blastocyst" is used in this disclosure to mean a mammalian embryo in which cellular differentiation has occurred consisting of an inner cell mass or embryoblast, a cavity, and an outer layer or trophoblast.

Salts of the Present Disclosure

The present disclosure relates to salts of Formula (I), and enantiomers, stereoisomers, and tautomers thereof, which are useful for the treatment of diseases and disorders associated with aging and cellular restoration such as age related infertility.

In some embodiments, the salt of Formula I has the structure of Formula (Ia) Ia:

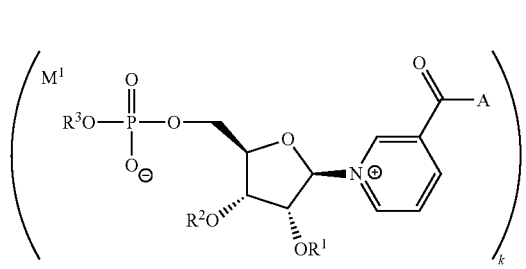

In some embodiments, the salt of Formula I has the structure of Formula Ib:

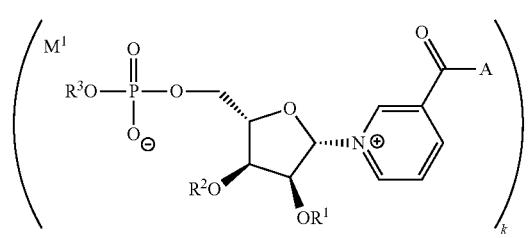

In some embodiments, the salt of Formula I has the structure of Formula Ic:

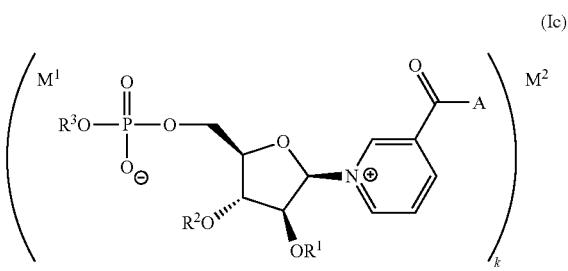

In some embodiments, the salt of Formula I has the structure of Formula Id:

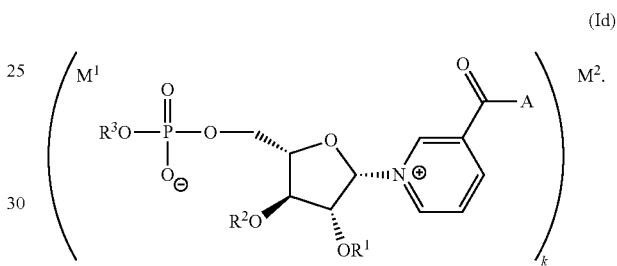

In some embodiments, the salt of Formula I has the structure of Formula Ie:

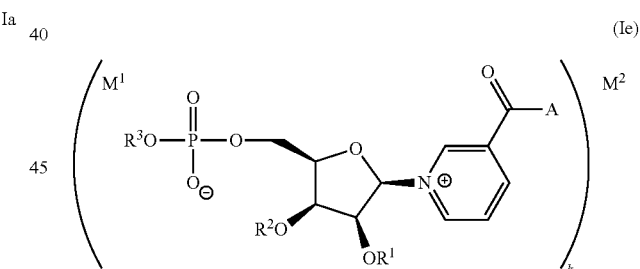

In some embodiments, the salt of Formula I has the structure of Formula If:

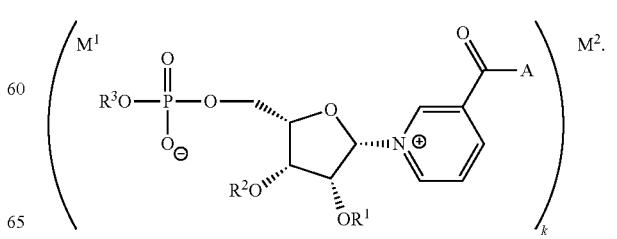

In some embodiments, the salt of Formula I has the structure of Formula Ig:

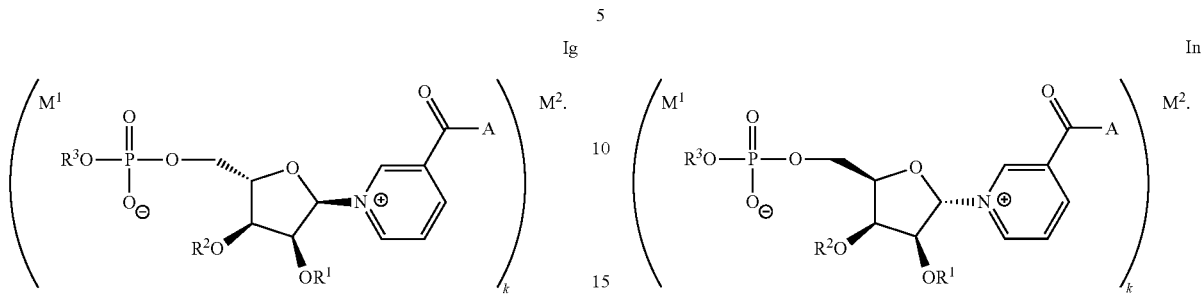

Ig

In some embodiments, the salt of Formula I has the structure of Formula Ik:

Ik

In some embodiments, the salt of Formula I has the structure of Formula Il:

Il

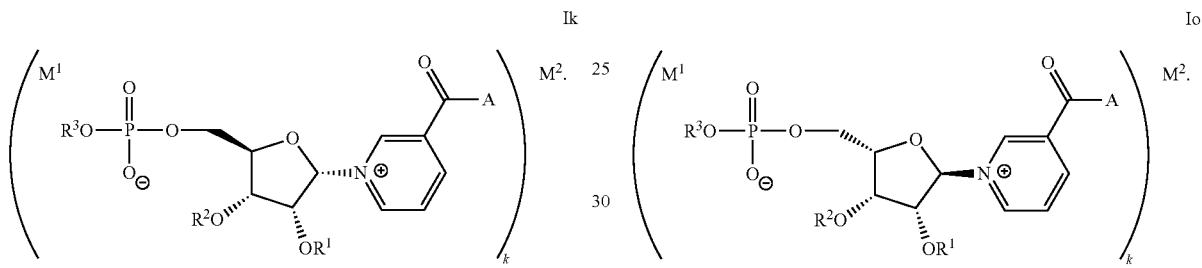

In some embodiments, the salt of Formula I has the structure of Formula Im:

Im

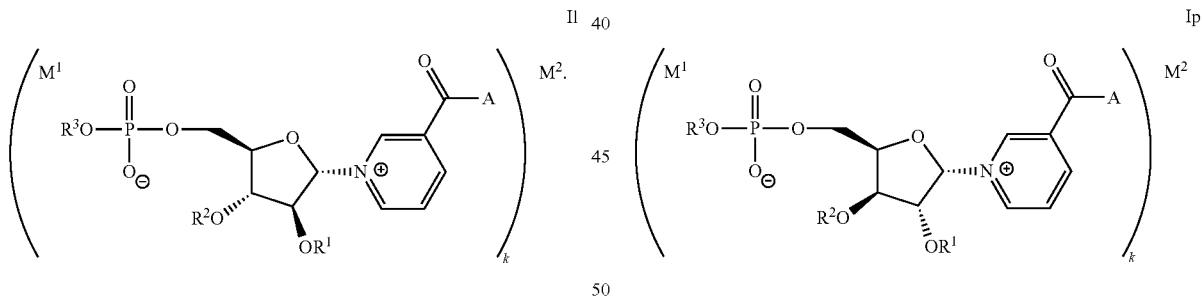

In some embodiments, the salt of Formula I has the structure of Formula In:

In

In some embodiments, the salt of Formula I has the structure of Formula Io:

Io

In some embodiments, the salt of Formula I has the structure of Formula Ip:

Ip

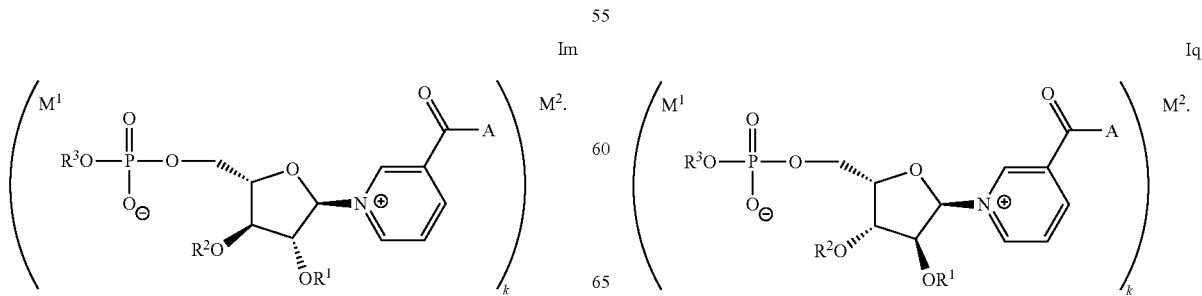

In some embodiments, the salt of Formula I has the structure of Formula Iq;

Iq

In some embodiments, the salt of Formula I has the structure of Formula Ir:

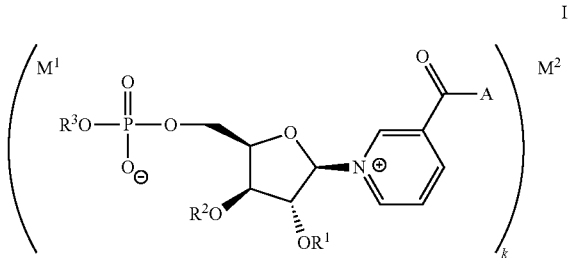

In some embodiments, the salt of Formula I has the structure of Formula Is:

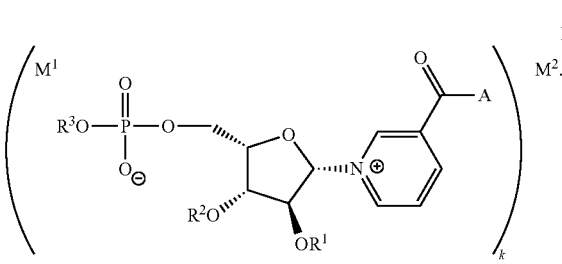

In one embodiment of the salt of Formula I, A is O$^-$.

In another embodiment of the salt of Formula I, $M^1$ and $M^2$ are cations. In another embodiment, $M^1$ and $M^2$ are cationic atoms. In another embodiment, $M^1$ and $M^2$ are, but not limited to, Li$^+$, Na$^+$, K$^+$, Rb$^+$, Cs$^+$, Be$^{2+}$, Mg$^{2+}$, Ca$^{2+}$, Sr$^{2+}$, Zn$^{2+}$, and Ba$^{2+}$. In another embodiment, $M^2$ is Li$^+$. In another embodiment, $M^1$ and $M^2$ are Na$^+$. In another embodiment, $M^1$ and $M^2$ are K$^+$. In another embodiment, $M^2$ is Rb$^+$. In another embodiment, $M^2$ is Cs$^+$. $M^1$ and $M^2$ can also be divalent cations such as Ca$^{2+}$, Be$^{2+}$, Mg$^{2+}$, Ca$^{2+}$, Sr$^{2+}$, Zn$^{2+}$, and Ba$^{2+}$. In one embodiment, $M^2$ is Ca$^{2+}$.

In some embodiments of the invention, $R^a$ is independently, at each occurrence H, or C$_1$-C$_6$alkyl. In other embodiments, $R^a$ is H. In other embodiments, $R^a$ is C$_1$-C$_6$alkyl. In other embodiments, $R^a$ is C$_1$-C$_6$alkyl substituted with one or more substituents selected from C$_1$-C$_6$alkyl, C$_2$-C$_6$alkenyl, C$_2$-C$_6$alkynyl, (C$_0$-C$_3$alkylene)C$_3$-C$_8$cycloakyl, (C$_0$-C$_3$alkylene)heterocycloakyl, (C$_0$-C$_3$alkylene)C$_6$-C$_{14}$aryl, or (C$_0$-C$_3$alkylene)heteroaryl. In other embodiments, $R^a$ is C$_1$-C$_6$alkyl substituted with one or more substituents selected from C$_1$-C$_6$alkyl. In other embodiments, $R^a$ is C$_1$-C$_6$alkyl substituted with one or C$_2$-C$_6$alkenyl. In other embodiments, $R^a$ is C$_1$-C$_6$alkyl substituted with one or more C$_2$-C$_6$alkynyl. In other embodiments, $R^a$ is C$_1$-C$_6$alkyl substituted with one or more (C$_0$-C$_3$alkylene)C$_3$-C$_8$cycloakyl. In other embodiments, $R^a$ is C$_1$-C$_6$alkyl substituted with one or more (C$_0$-C$_3$alkylene)heterocycloakyl. In other embodiments, $R^a$ is C$_1$-C$_6$alkyl substituted with one or more (C$_0$-C$_3$alkylene)C$_6$-C$_{14}$aryl. In other embodiments, $R^a$ is C$_1$-C$_6$alkyl substituted with one or more (C$_0$-C$_3$alkylene)heteroaryl. In other embodiment R is methyl. In other embodiment $R^a$ is methyl substituted with one or more substituents selected from C$_1$-C$_6$alkyl, C$_2$-C$_6$alkenyl, C$_2$-C$_6$alkynyl, (C$_0$-C$_3$alkylene)C$_3$-C$_8$cycloakyl, (C$_0$-C$_3$alkylene)heterocycloakyl, (C$_0$-C$_3$alkylene)C$_6$-C$_{14}$aryl, or (C$_0$-C$_3$alkylene)heteroaryl.

Yet in another embodiment, $R^3$ is a negative charge, H, or C$_1$-C$_6$ alkyl. In one embodiment, $R^3$ represents a negative charge. In another embodiment, $R^3$ is H. In another embodiment, $R^3$ is C$_1$-C$_6$ alkyl.

In one embodiment of the salt of Formula I, $M^1$ is a cation. In another embodiment, $M^1$ is a cation atom. In another embodiment, $M^1$ is, but not limited to, Li$^+$, Na$^+$, K$^+$, Rb$^+$, Cs$^+$, Be$^{2+}$, Mg$^{2+}$, Ca$^{2+}$, Sr$^{2+}$, and Ba$^{2+}$. In another embodiment, $M^1$ is Li$^+$. In another embodiment, $M^1$ is Na$^+$. In another embodiment, $M^1$ is K$^+$. In another embodiment, $M^1$ is Rb$^+$. In another embodiment, $M^1$ is Cs$^+$. In another embodiment, $M^1$ is Ca$^{2+}$.

In a further embodiment, $R^1$ is independently H, C$_1$-C$_6$alkyl, C$_1$-C$_6$haloalkyl, (C$_0$-C$_3$alkylene)C(O)C$_1$-C$_6$alkyl, —C(O)OR$^a$, —C(O)NR$^a$R$^b$, or —[CH$_2$—CH$_2$—O]$_n$—R$^a$. In another embodiment, $R^1$ is H. In another embodiment, $R^1$ is C$_1$-C$_6$alkyl. In another embodiment, $R^1$ is C$_1$-C$_6$haloalkyl. In another embodiment, $R^1$ is (C$_0$-C$_3$alkylene)C(O)C$_1$-C$_6$alkyl. In another embodiment, $R^1$ is —C(O)OR$^a$. In another embodiment, $R^1$ is —[CH$_2$—CH$_2$—O]$_n$—R$^a$. In another embodiment, $R^1$ is C(O)C$_1$-C$_6$alkyl.

In one embodiment, $R^2$ is independently H, C$_1$-C$_6$alkyl, C$_1$-C$_6$haloalkyl, (C$_0$-C$_3$alkylene)C(O)C$_1$-C$_6$alkyl, —C(O)OR$^a$, —C(O)NR$^a$R$^b$, or —[CH$_2$—CH$_2$—O]$_n$—R$^a$. In another embodiment, $R^2$ is H. In another embodiment, $R^2$ is C$_1$-C$_6$alkyl. In another embodiment, $R^2$ is C$_1$-C$_6$haloalkyl. In another embodiment, $R^2$ is (C$_0$-C$_3$alkylene)C(O)C$_1$-C$_6$alkyl. In another embodiment, $R^2$ is —C(O)OR$^a$. In another embodiment, $R^2$ is —[CH$_2$—CH$_2$—O]—R$^a$. In another embodiment, $R^1$ is C(O)C$_1$-C$_6$alkyl.

In a further embodiment of the salts of the Formula I, $R^1$ and $R^2$, together with the atom to which they are attached, may form a 5-membered heterocyclic ring. In yet a further embodiment of the salts of the Formula I, $R^1$ and $R^2$, together with the atom to which they are attached, may form a 5-membered heterocyclic ring substituted with one or more substituents selected from C$_1$-C$_6$alkyl, C$_2$-C$_6$alkenyl, C$_2$-C$_6$alkynyl, (C$_0$-C$_3$alkylene)C$_3$-C$_8$cycloakyl, (C$_0$-C$_3$alkylene)heterocycloakyl, (C$_0$-C$_3$alkylene)C$_6$-C$_{14}$aryl, and (C$_0$-C$_3$alkylene)heteroaryl.

In another embodiment, n at each occurrence is 1, 2, 3, 4, 5, 6, 7, or 8. In another embodiment, n is 1. In another embodiment, n is 2. In another embodiment, n is 3. In another embodiment, n is 4. In another embodiment, n is 5. In another embodiment, n is 6. In another embodiment, n is 7. In another embodiment, n is 8.

In one embodiment, k is 1. In another embodiment, k is 2.

In another embodiment, the salt of Formula (I) is selected from the group:
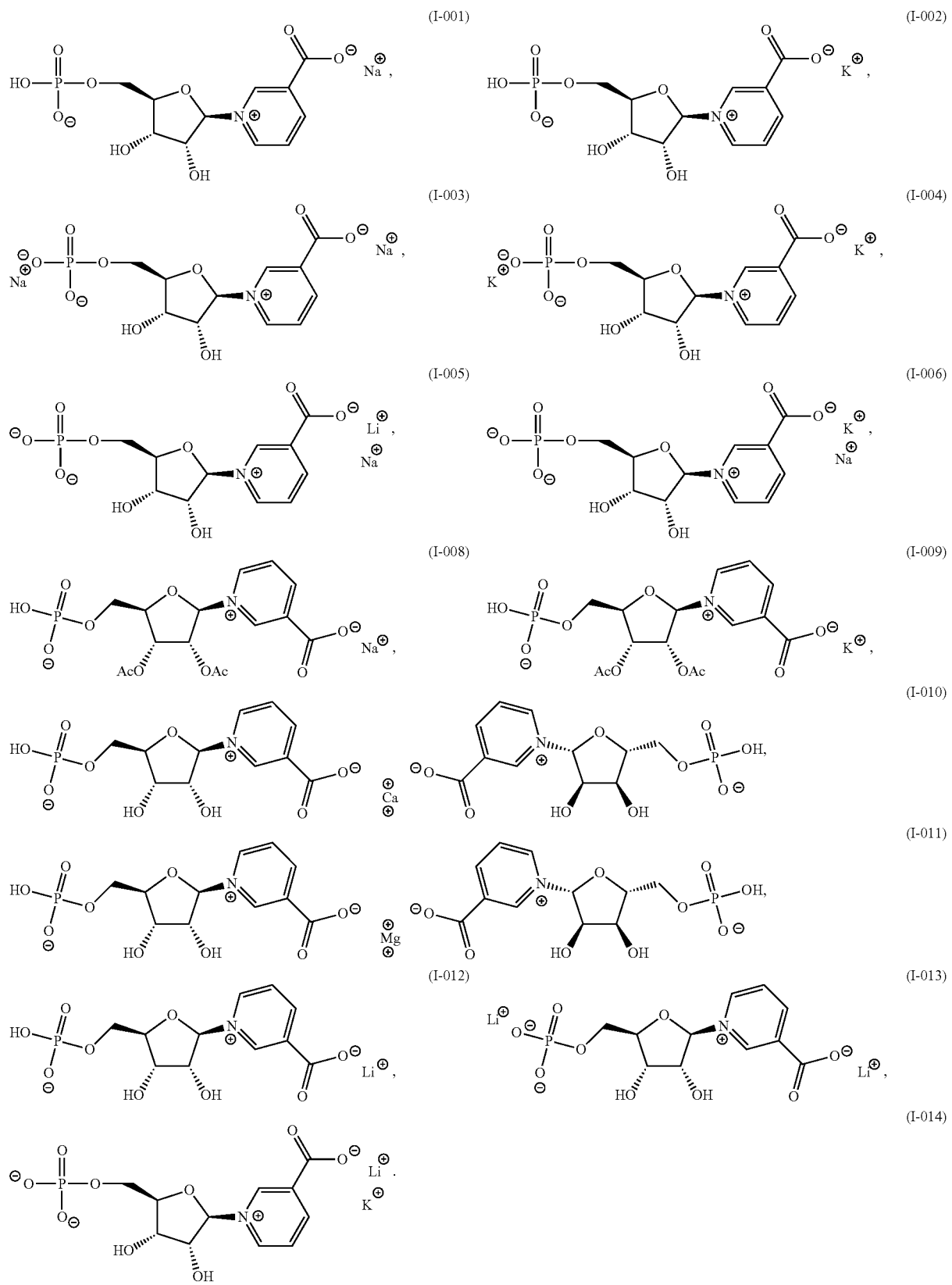

Method for Preparation of the Salts

The salts of the present disclosure may be made by a variety of methods, including standard chemistry. Suitable synthetic routes are depicted in the Schemes given below.

Another aspect of present disclosure relates to a process for preparing the salts of Formula (I). The process comprises contacting a nicotinic acid mononucleotide derivative of Formula (II) with a metal-alkali hydroxide under suitable conditions effective to produce the product salt of Formula (I)

In one embodiment, the process of preparing the instant salts involves nitrogenating the atmosphere under which the reaction occurs. In another embodiment, the first step in preparing the instant salts involves charging the nucleotide with nitrogen then adding deionized water to create a solution of NaMN. In one embodiment the second step involves adding the metal-alkali hydroxide dropwise to the resulting solution of NaMN to elevate the pH to about 6.5.

In one embodiment of the invention, the process of preparing the salt of Formula (I) involves contacting a compound of Formula (II)

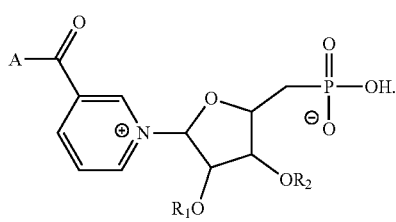

(II)

with a metal-alkali hydroxide under conditions effective to produce the salt of Formula (I).

In one embodiment, the metal-alkali hydroxide is selected from LiOH, NaOH, KOH, $Mg(OH)_2$, $Ca(OH)_2$, $Zn(OH)_2$, and $Ba(OH)_2$.

The process described herein provides an order of addition of the materials, reagents and reactants to not only achieve a high degree of purity of the salt of Formula (I), but also a stable form of the salt of Formula (I). The reversal of the order of addition described above, i.e. addition of solid mononucleotide (NaMN) to aqueous metal-alkali hydroxide leads to a substantially impure product which is susceptible to premature degradation. Thus the formation of the salts is not an inevitable consequence of simply mixing the materials, reagents and reactants in any order, rather the described step-wise addition appears to produce a more stable and soluble salt of Formula (I) as compared to products produced by mixing the reagents in the reverse order.

Although not wishing to be limited by theory it is hypothesized that the glycosidic bond of the salt of Formula I is susceptible to an increased risk of degradation under the conditions resulting from the addition of solid NaMN to aqueous base yielding a substantially impure product comprising of the degradation products nicotinamide and ribose rather than the desired product of acceptable purity.

The instant disclosure also envisions analogous methods to prepare the salts of Formula (I), known in the art of organic synthesis as set forth in part by the following synthetic scheme 1.

Those skilled in the art will recognize if a stereocenter exists in the salts of Formula (I). Accordingly, the present includes both possible stereoisomers (unless specified in the synthesis) and includes not only racemic salts but the individual enantiomers and/or diastereomers as well. When a compound or salt is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The salts and compounds described herein may be made from commercially available starting materials or synthesized using known organic, inorganic, and/or enzymatic processes.

The salts of Formula (I) can be prepared in a number of ways well known to those skilled in the art of organic synthesis. By way of example, salts of Formula (I) can be synthesized using the methods described below, together with synthetic methods known in the art of synthetic organic chemistry, or variations thereon as appreciated by those skilled in the art. These methods include but are not limited to those methods described below. Salts of Formula (I) can be synthesized by following the steps outlined in General Scheme 1 which comprises a sequence of assembling various intermediates. Starting materials are either commercially available or made by known procedures in the reported literature or as illustrated.

Scheme 1

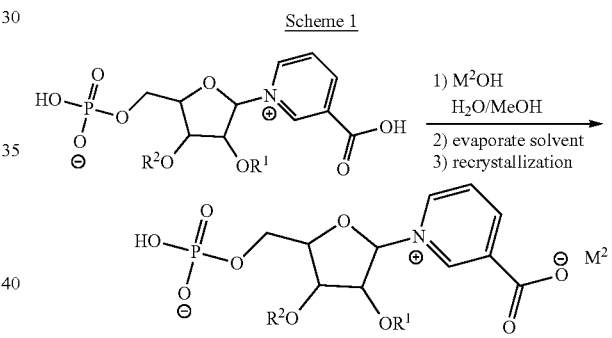

The salts of Formula (I) described herein can be prepared according to the general procedures outlined in Scheme 1. A condensation of the precursor and commercially available nicotinic acid mononucleotide is generally done with a metal-alkali hydroxide in presence of suitable solvent (e.g., a mixture of methanol and water). The mixture is heated to slowly evaporate the solvents. The resulting mixture may also be freeze-dried to obtain the desired product salt under suitable conditions of temperature and pressure.

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the groups $M^+$ represent $M^1$ and $M^2$ and other variables are as defined above, except where otherwise indicated. Furthermore, for synthetic purposes, the salts of General Scheme 1 are mere representative with elected radicals to illustrate the general synthetic methodology of the salts of Formula (I) as defined herein.

It is also understood that the salts disclosed herein possess a neutral electrical charge and that the structure of Formula I is only a representative of genus, which, if necessary, may be balanced with a counterion to allow the salt to present a neutral electrical charge. Such counterions may include, without limitation, bromine, chlorine, and triflates. In one embodiment, the salt of this disclosure can be generated in situ without the need to isolate from solution. In some embodiments, the salts contemplated herein can be discrete 1:1 or 1:2 salts. The salts described herein can also exist in other ratios, e.g., 1:1.5, 1:5, and 1:10.

Methods of Using the Salts

Another aspect of the present disclosure relates to a method of treating or preventing a disease or disorder associated with aging, cellular degradation, and/or cellular restoration. Non limiting examples of such diseases and disorders include infertility, age related infertility, age-related loss of eye function, reduction in bone density, obesity and insulin insensitivity. In one embodiment, the salts of Formula (I) are useful in the treatment of age related infertility. In another embodiment the salts of Formula (I) are useful in the treatment of fertility.

Another aspect of the present disclosure relates to a method of treating or preventing an age-related disease or disorder. The method comprises administering to a subject in need thereof a therapeutically effective amount of a pharmaceutical composition of the salt of Formula I.

Yet another aspect of the present disclosure relates to the method of improving oocyte or blastocyst quality and maturation. The method comprises contacting the oocyte or blastocyst for an effective period of time with IVF media comprising a salt of Formula (I).

In another aspect, the present disclosure provides media containing a salt of Formula (I). The salts of Formula (I) have shown surprising and unexpected prolonged stability in solution and thus are useful in media for exposing eggs, oocytes and/or blastocytes for periods of time necessary for enhancing NAD$^+$ production prior to implantation into a subject suffering from infertility or age-related infertility. In some embodiments, media comprising a salt of Formula (I) is provided. In some embodiments the media comprises the various reagents and factors necessary for the egg, oocyte or blastocyst depending on which stage of maturation and development the egg, oocyte or blastocyst is in. For example, the media can contain any of the agents or factors useful in IVF media listed in Table 1 below:

TABLE 1

CULTURE MEDIA COMPONENTS

Inorganic salts
Energy substrates
(glucose, pyruvate and lactate)
Essential amino acids
(arginine, cysteine, glutamine, histidine, isoleucine, leucine, lysine, methionine,
phenylalanine, threonine, tryptophan, tyrosine and valine)
Nonessential amino acids
(alanine, asparagine, asparatate, glycine, glutamate, proline and serine)
Chelators
pH indicators
Antibiotic agents
(such as combination of penicillin and streptomycin)
Serum albumin
Vitamins
Growth factors
(insulin or GM-CSF, among others)

Also provided is a cell culture medium for in vitro fertilization comprising: one or more salts of Formula (I) and culturing agents.

In one embodiment, the culturing agent is an inorganic salt, an energy substrate, an amino acid, a chelator, a pH indicator, an antibiotic, a serum, a vitamin, a growth factor, or any combination thereof. In one embodiment, the inorganic salt is calcium chloride, magnesium chloride, magnesium sulfate, potassium chloride, sodium bicarbonate, sodium chloride, monosodium phosphate, disodium phosphate, or any combination thereof.

In one embodiment, the energy substrate is glucose, pyruvate, lactate, pyruvate, or any combination thereof.

In one embodiment, the amino acid is an essential amino acid. In one embodiment, the essential amino acid is arginine, cysteine, glutamine, glycine, histidine, isoleucine, leucine, lysine, methionine, phenylalanine, proline, threonine, tryptophan, tyrosine, valine, or any combination thereof.

In one embodiment, the amino acid is a non-essential amino acid.

In one embodiment, the non-essential amino acid is alanine, asparagine, aspartate, glutamate, proline, serine, or any combination thereof.

In one embodiment, the chelator is clathro chelate, acetyl acetone, amino polycarboxylic acid, ATMP, BAPTA, BDTH2, citric acid, cryptand, deferasirox, 2,3-dihydrobenzoic acid, 2,3-dimercapto-1-propane sulfonic acid, dimercapto succinic acid, DOTA, DTPMP, EDDHA, EDDS, EDTMP, etidronic acid, fura-2, gluconic acid, homocitric acid, imino diacetic acid, Indo-1, nitrile triacetic acid, pentetic acid (DTPA), phosphonate, phytochelati, poly aspartic acid, sodium poly aspartate, trisodium citrate, transferrin, EDTA, EGTA, or any combination thereof.

In one embodiment, the pH indicator is phenol red, bromothymol blue, alizarin red, 9-aminoacridine, or any combination thereof.

In one embodiment, the antibiotic is actinomycin D, ampicillin, carbenicillin, cefotaxime, fosmidomycin, gentamicin, kanamycin, neomycin, penicillin, polymyxin B, streptomycin, or any combination thereof.

In one embodiment, the serum is human serum albumin, bovine serum albumin, fetal bovine serum, synthetic serum, or any combination thereof.

In one embodiment, the vitamin is ascorbic acid, biotin, menadione sodium bisulfite, mitomycin C, pyridoxamine dihydrochloride, retinyl acetate, (−)-riboflavin, (+)-sodium L-ascorbate, (+)-α-tocopherol, vitamin $B_{12}$, thiamine hydrochloride, i-inositol, pyridoxal hydrochloride, nicotinamide, folic acid, D-calcium pantothenate, choline chloride, or any combination thereof.

In one embodiment, the growth factor is adrenomedullin, angiopoietin, bone morphogenetic proteins, macrophage colony-stimulating factor (M-CSF), granulocyte colony-stimulating factor (G-CSF), granulocyte macrophage colony-stimulating factor (GM-CSF), epidermal growth factor, ephrins, erythropoietin, gibroblast growth factor, growth differentiation factor-9, hepatocyte growth factor, insulin, insulin-like growth factors, interleukins, keratinocyte growth factor, migration-stimulating factor, macrophage-stimulating protein, myostatin, neurotrophins, t-cell growth factor, thrombopoietin, transforming growth factor, tumor necrosis factor-alpha, vascular endothelial growth factor, or any combination thereof.

In one embodiment, the cell culture medium further comprises an oocyte, zygote, blastocyst, or any combination thereof Also, provided are kits for IVF media comprising various agents, and factors necessary for oocyte or blastocyst maturation including one or more salts of Formula (I). These agents and cofactors can be dissolved in solution to create the IVF media shortly before use in exposing an oocyte or blastocyst prior to implanting into a patient in need of treatment for infertility or age-related infertility.

The present invention also relates to the use of the salts of Formula I and enantiomers, stereoisomers, and tautomers thereof for the manufacture of medicaments for treating aging, cellular restoration, cellular degradation, or infertility. In certain embodiments the infertility treated is age-related infertility.

Another aspect of the present invention is a pharmaceutical composition comprising the salt of Formula I and a pharmaceutically acceptable carrier.

Another aspect of the present invention is a pharmaceutical composition comprising the salt of Formula I and a pharmaceutically acceptable carrier comprising therapeutically effective amounts of one or more additional therapeutic agents.

In some embodiments, administration of a salt of Formula (I) or a pharmaceutical composition comprising a salt of the present invention and a pharmaceutically acceptable carrier induces a change in the cell cycle or cell viability.

In some embodiments, administration of a salt of Formula (I) or a pharmaceutical composition comprising a salt of the present invention and a pharmaceutically acceptable carrier induces a prophylactic change in the disorder or disease associated with aging.

Administration of the disclosed salts can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Pharmaceutical compositions can be prepared according to conventional mixing, granulating or coating methods, respectively, and the present pharmaceutical compositions can contain from about 0.1% to about 99%, from about 5% to about 90%, or from about 1% to about 20% of the disclosed salt by weight or volume.

In one embodiment, the present invention relates to a method of preparing a pharmaceutical composition of the present invention by mixing at least one pharmaceutically acceptable salt of the present invention, and, optionally, one or more pharmaceutically acceptable carriers, additives, or excipients.

In another embodiment, the present invention relates to a method of preparing a pharmaceutical composition of the present invention by mixing at least one pharmaceutically acceptable salt of the present invention and one or more additional therapeutic agents.

Effective dosage amounts of the salts of Formula (I), when used in the described methods, range from about 0.5 mg to about 5000 mg of the disclosed salt as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed salt or, in a range of from one amount to another amount in the list of doses. In one embodiment, the compositions are in the form of a tablet that can be scored.

The dosage regimen utilizing the disclosed salt is selected in accordance with a variety of factors including type, species, age, weight, sex and medical condition of the patient; the severity of the condition to be treated; the route of administration; the renal or hepatic function of the patient; and the particular disclosed salt employed. A physician or veterinarian of ordinary skill in the art can readily determine and prescribe the effective amount of the drug required to prevent, counter or arrest the progress of the condition.

Illustrative pharmaceutical compositions are tablets and gelatin capsules comprising a salt of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the salt such as cyclodextrin, hydroxypropyl-cyclodextrin, PEG400, PEG200.

For preparing pharmaceutical compositions from the salts of Formula (I), inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed salt is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The following salts disclosed herein were prepared using the general synthetic methodology including without limitation reagents such as NaOH, LiOH, or KOH. Suitable solvents such as methanol, ethanol, water, acetic acid, ethylene glycol, isopropanol were also used.

Abbreviations used in the following examples and elsewhere herein are:

AcOH acetic acid
anh. anhydrous
atm atmosphere
aq. aqueous
br broad
Boc tert-butyloxycarbonyl
brine saturated aqueous sodium chloride
n-BuLi n-butyllithium
n-BuOH n-butanol
Calc'd calculated
$CDCl_3$ deuterated chloroform
CDI carbonyldiimidazole
Chloroform-d deuterated chloroform
d doublet
dd doublet of doublets
dt doublet of triplets
$D_2O$ deuterated water (deuterium oxide)
DCE dichloroethane
DCM dichloromethane
DIAD diisopropyl azodicarboxylate
DIPEAN, N-diisopropylethylamine
DMAc N,N-dimethyl acetamide
DMAPN, N-dimethylpyridin-4-amine
DME 1,2-dimethoxyethane
DMEDA N,N'-dimethylethylenediamine
DMF N,N-dimethylformamide
DMSO dimethyl sulfoxide
DMSO-$d_6$ deuterated dimethyl sulfoxide
EDA ethylenediamine
EDC 1-ethyl-3-(3-dimethylaminopropyl)carbodiimide
$Et_2O$ diethyl ether
EtOAc ethyl acetate
EtOH ethanol
ESI electrospray ionization
g gram
h hour(s)
H hydrogen
$^1H$ NMR nuclear magnetic resonance (proton nucleus)
HATU [bis(dimethylamino)methylene]-1H-1,2,3-triazolo[4,5-b]pyridinium 3-oxide hexafluorophosphate
HBTU 3-[bis(dimethylamino)methylene]-3H-benzotriazol-1-oxide hexafluorophosphate
HOBt hydroxybenzotriazole
HPLC high pressure (or performance) liquid chromatography
Hz hertz
J coupling constant
$KHCO_3$ potassium bicarbonate
KHMDS potassium hexamethyldisilazide
KOAc potassium acetate
LCMS liquid chromatography mass spectrometry
LHMDS lihtium hexamethyldisilazide
[#] M molar concentration
m multiplet
$[M+H]^+$ molecular ion plus hydrogen
$[M-tBu+H]^+$ molecular ion minus tert-butyl plus hydrogen
mCPBA meta-chloroperoxybenzoic acid
$Me_2NH$ dimethylamine
$Me_4NBr$ tetramethylammonium bromide
MeCN acetonitrile
$MeNH_2$ methylamine
MeOH methanol
Methanol-$d_4$ deuterated methanol
2-MeTHF 2-methyl tetrahydrofuran
mg milligram
MHz megahertz
min min
mmol millimole
mL milliliter
MS mass spectrometry
MS ES mass spectrometry electrospray
$Ms_2O$ methanesulfonic anhydride
MTBE methyl tert-butyl ether
MW microwave
m/z mass-to-charge ratio
µL microliter
$N_2$ nitrogen
$NaHCO_3$ sodium bicarbonate
NaMN nicotinic acid mononucleotide
NIS N-iodosuccinimide
NMP N-methyl-2-pyrrolidone
NMR nuclear magnetic resonance
PEPPSI-iPr [1,3-bis(2,6-diisopropylphenyl)imidazol-2-ylidene](3-chloropyridyl)palladium(II) dichloride
$PdCl_2$(Amphos) bis(di-tert-butyl(4-dimethylaminophenyl)phosphine) dichloropalladium(II)
$Pd_2(dba)_3$ tris(dibenzylideneacetone)dipalladium(0)
$Pd(OAc)_2$ palladium(II) acetate
$PdCl_2$(dppf) [1,1'-bis(diphenylphosphino)ferrocene]dichloropalladium(II)
$PdCl_2(MeCN)_2$ bis(acetonitrile)dichloropalladium(II)
$PdCl_2(PPh_3)_2$ bis(triphenylphosphinepalladium(II) dichloride
$Pd(P(Cy)_3)_2Cl_2$ dichlorobis(tricyclohexylphosphine)palladium(II)

Pd(PPh$_3$)$_4$ tetrakis(triphenylphosphine)palladium(0)
Pd(t-Bu$_3$P)$_2$ bis(tri-tert-butylphosphine)palladium(0)
pH potential of hydrogen
PMB 4-methoxybenzyl
PMBCl 4-methoxybenzyl chloride
ppm parts per million
prep preparative
py pyridine
q quartet
qd quartet of doublets
quant. quantitative
quin. quintuplet
quind quintuplet of doublets
RBF round-bottom flask
Rt retention time
rt room temperature
s singlet
sat. saturated
sat. aq. saturated aqueous
SEMCl 2-(trimethylsilyl)ethoxymethyl chloride
t triplet
t-BuLi tert-butyllithium
td triplet of doublets
TMS trimethylsilyl
TMSCl trimethylsilyl chloride
tt triplet of triplets
T3P polyphosphonic anhydride
TBAB tetrabutylammonium bromide
TEA triethylamine
TFA trifluoroacetic acid
TFAA trifluoroacetic anhydride
THF tetrahydrofuran
TLC thin layer chromatography
TPPO triphenylphosphine oxide
XantPhos 4,5-bis(diphenylphosphino)-9,9-dimethylxanthene
XPhos 2-dicyclohexylphosphino-2',4',6'-triisopropylbiphenyl Example 1. Synthesis of Sodium 1-((2R,3R,4S,5R)-5-(((hydrogenphosphonato)oxy)methyl)-3,4-dihydroxytetrahydrofuran-2-yl)pyridine-1-ium-3-carboxylate (I-001)

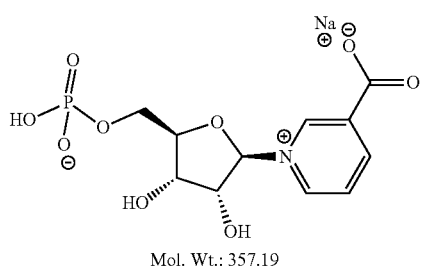

Mol. Wt.: 357.19

A 50 mL 3 N RBF fitted with a water condenser, rubber septum and internal thermometre was charged with NaMN (0.200 g, 0.298 mmol, 1 eq) and 5 ml of distilled deionised water and mixed to form a solution. This solution was cooled using an ice/water bath to bring the internal temperature below 10° C. (pH of solution=1.8) To this solution was then added dropwise 2.83 ml of 0.1M NaOH solution slowly via syringe so as to prevent the temperature from increasing. After this addition the pH was 3.9. A further 0.1 ml of NaOH solution was then added and the pH moved to 4.6. The flask was then removed, and the solution transferred to a single neck flask and the water removed via Kugel Rhor distillation at 45° C. external (temperatures above this lead to degradation of the product). This will slowly remove water. Make sure the receiving flasks are cooled and when there is ~1 ml of solvent left in the distillation pot, take the temperature of the oven down to room temperature. Once dried the product is rendered as a colourless solid. Yield: 78.6 mg (74%); Melting point: 74-79° C. (degradation, corrected) outgassing at 130° C. $^1$H-NMR (400 MHz, D$_2$O) δ=9.35 (s, 1H), 9.26 (d, 1H), 8.98 (d, 1H), 8.25 (t, 1H), 6.23 (d, 1H), 4.65 (p, 1H), 4.57 (t, 1H), 4.48 (m, 1H), 4.33 (dq, 1H), 4.19 (dq, 1H) ppm Example 2. Synthesis of Potassium 1-((2R,3R,4S,5R)-5-(((hydrogenphosphonato)oxy)methyl)-3,4-dihydroxytetrahydrofuran-2-yl)pyridine-1-ium-3-carboxylate (I-002)

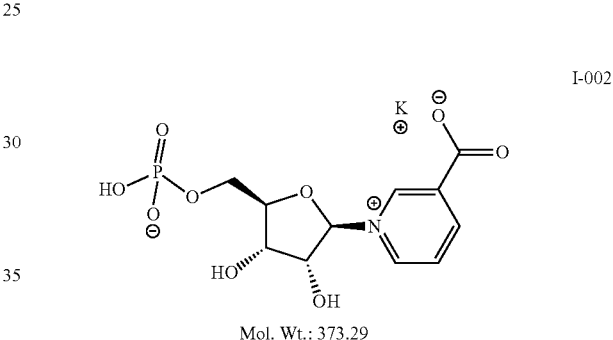

Mol. Wt.: 373.29

A 50 mL 3 N RBF fitted with a water condenser and internal thermometer was charged with NaMN (0.200 g, 0.298 mmol, 1 eq) and 5 ml of distilled deionised water and mixed to form a solution. This solution was cooled using an ice/water bath to bring the internal temperature below 10° C. (pH of solution=1.8) To this solution was then added dropwise 2.83 ml of 0.1M KOH solution slowly so as to prevent the temperature from increasing. After this addition the pH was 2.8. A further 0.2 ml of KOH solution was then added and the pH moved to 3.9. The flask was then removed and the solution transferred to a single neck flask and the water removed via Kugel Rhor distillation at 45° C. external (temperatures above this lead to degradation of the product). This will slowly remove water. Make sure the receiving flasks are cooled and when there is ~1 ml of solvent left in the distillation pot, take the temperature of the oven down to room temperature. Once dried the product is rendered as a colourless solid. Yield: 72.5 mg (65%); Melting point: 71-78° C. (degradation, corrected) outgassing at 130° C.). $^1$H-NMR (400 MHz, D$_2$O) δ=9.35 (s, 1H), 9.26 (d, 1H), 8.98 (d, 1H), 8.24 (t, 1H), 6.23 (d, 1H), 4.65 (p, 1H), 4.56 (t, 1H), 4.47 (m, 1H), 4.33 (dq, 1H), 4.19 (dq, 1H) ppm

Example 3. Synthesis of Sodium 1-((2R,3R,4S,5R)-3,4-dihydroxy-5-((phosphonatooxy)methyl)-tetrahydrofuran-2-yl)pyridine-1-ium-3-carboxylate (I-003)

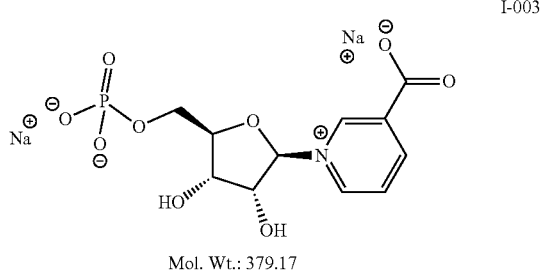 [SMILES: [Na+] ; [Na+] ; O=C([O-])c1ccc[n+]([C@@H]2O[C@H](COP(=O)([O-])[O-])[C@@H](O)[C@H]2O)c1]

Mol. Wt.: 379.17

A 50 mL 3 N RBF fitted with a water condenser, rubber septum and internal thermometer was charged with NaMN (0.200 g, 0.597 mmol, 1 eq) and 5 ml of distilled deionised water and mixed to form a solution. This solution was cooled using an ice/water bath to bring the internal temperature below 10° C. (pH of solution=1.8) To this solution was then added dropwise 11.9 ml of 0.1 M NaOH (aq) solution via syringe so as to prevent the temperature from increasing. The flask was then removed and the solution transferred to a single neck flask and the water removed via Kugel Rhor distillation with an oil pump pulling below 0.5 mBar, with rotation at 28° C. external (temperatures above this lead to degradation of the product) for 6 hours. This will slowly remove water. The liquid inside the reaction flask will freeze and once dried the product is rendered as a colourless solid. Yield: 173 mg (77%); Melting point: 96-100° C. (degradation, corrected) outgassing at 130° C.). $^1$H-NMR (400 MHz, $D_2O$) δ=9.48 (d, 1H), 9.22 (s, 1H), 8.93 (d, 1H), 8.26 (t, 1H), 6.18 (d, 1H), 4.61 (t, 1H), 4.56 (p, 1H), 4.47 (dd, 1H), 4.16 (dq, 1H), 4.05 (dq, 1H) ppm

Example 4. Synthesis of Potassium 1-((2R,3R,4S,5R)-3,4-dihydroxy-5-((phosphonatooxy)methyl)-tetrahydrofuran-2-yl)pyridine-1-ium-3-carboxylate (I-004)

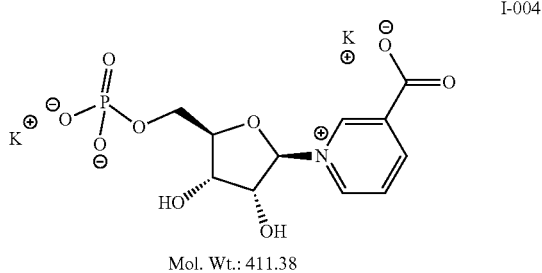 [SMILES: [K+] ; [K+] ; O=C([O-])c1ccc[n+]([C@@H]2O[C@H](COP(=O)([O-])[O-])[C@@H](O)[C@H]2O)c1]

Mol. Wt.: 411.38

A 50 mL 3 N RBF fitted with a water condenser, rubber septum and internal thermometer was charged with NaMN (0.200 g, 0.597 mmol, 1 eq) and 5 ml of distilled deionised water and mixed to form a solution. This solution was cooled using an ice/water bath to bring the internal temperature below 10° C. (pH of solution=1.8) To this solution was then added dropwise 11.9 ml of 0.1 M KOH (aq) solution via syringe so as to prevent the temperature from increasing. The flask was then removed and the solution transferred to a single neck flask and the water removed via Kugel Rhor distillation using an oil pump pulling below 0.5 mBar and with rotation at 28° C. external (temperatures above this lead to degradation of the product) for 6 hours. This will slowly remove water. The liquid inside the reaction flask will freeze and once dried the product is rendered as a colourless solid. Yield: 194.4 mg (79%); Melting point: 94-100° C. (degradation, corrected) outgassing at 130° C.). $^1$H-NMR (400 MHz, $D_2O$) δ=9.45 (d, 1H), 9.28 (s, 1H), 8.96 (d, 1H), 8.29 (t, 1H), 6.22 (d, 1H), 4.65-4.58 (m, 2H), 4.48 (dd, 1H), 4.22 (dq, 1H), 4.09 (dq, 1H) ppm

Example 5. Synthesis of Potassium sodium 1-((2R,3R,4S,5R)-3,4-dihydroxy-5-((phosphonatooxy)methyl)tetrahydrofuran-2-yl)pyridine-1-ium-3-carboxylate (I-006)

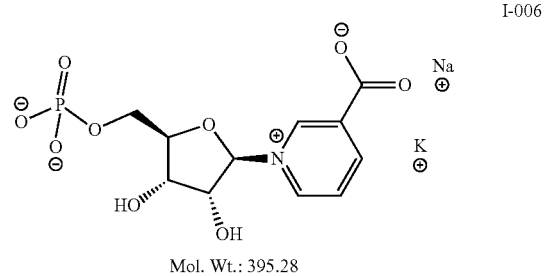 [SMILES: O=C([O-])c1ccc[n+]([C@@H]2O[C@H](COP(=O)([O-])[O-])[C@@H](O)[C@H]2O)c1 ; [K+] ; [Na+]]

Mol. Wt.: 395.28

A 50 mL 3 N RBF fitted with a water condenser and internal thermometer was charged with NaMN (0.300 g, 0.895 mmol, 1 eq) and 15 ml of distilled deionised water and mixed to form a solution. This solution was cooled using an ice/water bath to bring the internal temperature below 5° C. To this solution was then added dropwise 8.95 ml of 0.1M KOH solution slowly so as to prevent the temperature from increasing, following this addition 8.95 ml of 0.1M NaOH solution was added dropwise to keep the temperature below 5° C. After this addition the pH was 6.8-7.0. The flask was then removed and the colourless solution frozen using liquid nitrogen. While the flask was frozen it was connected to the freeze dryer. This will slowly remove water. Once dried the product is rendered as a faint pink solid. Yield: 348.2 mg (near quantitative yield); Melting point: 86.3-94.1° C. (degradation, corrected) outgassing at 130° C.). $^1$H-NMR (400 MHz, $D_2O$) δ=9.48 (d, 1H), 9.28 (s, 1H), 8.95 (d, 1H), 8.29 (dd, 1H), 6.21 (d, 1H), 4.62 (t, p, 2H), 4.50 (m, 1H), 4.20 (dq, 1H), 4.08 (dq, 1H) ppm Example 6. Synthesis of Sodium 1-((2R,3R, 4R, 5R)-3,4-diacetoxy-5-(((hydrogenphosphonato)oxy)methyl)tetrahydrofuran-2-yl)pyridine-1-ium-3-carboxylate (I-008)

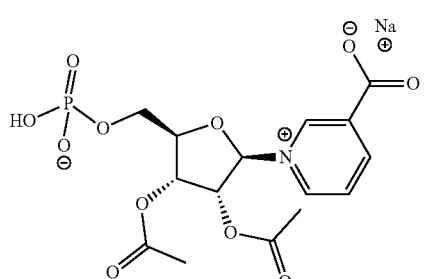

I-008

Mol. Wt.: 441.26

A 50 mL 3 N RBF fitted with a water condenser and internal thermometer was charged with ((2R,3R,4R,5R)-3,4-Diacetoxy-5-(3-carboxypyridin-1-ium-1-yl)tetrahydrofuran-2-yl)methyl hydrogen phosphate (0.050 g, 0.119 mmol, 1 eq) and 2 ml of distilled deionised water and mixed to form a solution. This solution was cooled using an ice/water bath to bring the internal temperature below 10° C. To this solution was then added dropwise 1.13 ml of 0.1M NaHCO$_3$ solution slowly so as to prevent the temperature from increasing. The flask was then removed and the colourless solution frozen using liquid nitrogen. While the flask was frozen it was connected to the freeze dryer. This will slowly remove water. Once dried the product is rendered as a colourless to faint yellow solid. Yield: 47.6 mg (90% yield); Melting point: 78-85° C. (degradation, corrected) outgassing at 128° C. $^1$H-NMR (400 MHz, D$_2$O) δ=9.38 (s, 1H), 9.32 (d, 1H), 9.01 (d, 1H), 8.28 (dd, 1H), 6.63 (d, 1H), 5.65 (m, 2H), 4.40 (m, 1H), 4.25 (dq, 1H), 2.23 (2×s, 6H) ppm Example 7. Synthesis of potassium 1-((2R,3R, 4R, 5R)-3,4-diacetoxy-5-(((hydrogenphosphonato)oxy)methyl)tetrahydrofuran-2-yl)pyridine-1-ium-3-carboxylate (I-009)

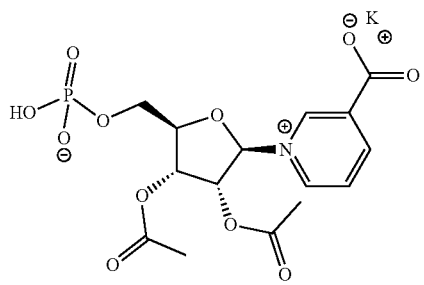

I-009

Mol. Wt.: 457.37

A 50 mL 3 N RBF fitted with a water condenser and internal thermometer was charged with ((2R,3R,4R,5R)-3,4-Diacetoxy-5-(3-carboxypyridin-1-ium-1-yl)tetrahydrofuran-2-yl)methyl hydrogen phosphate (0.050 g, 0.119 mmol, 1 eq) and 2 ml of distilled deionised water and mixed to form a solution. This solution was cooled using an ice/water bath to bring the internal temperature below 10° C. To this solution was then added dropwise 1.13 ml of 0.1M KHCO$_3$ solution slowly so as to prevent the temperature from increasing. The flask was then removed and the colourless solution frozen using liquid nitrogen. While the flask was frozen it was connected to the freeze dryer. This will slowly remove water. Once dried the product is rendered as a colourless to faint yellow solid. Yield: 45.3 mg (83% yield); Melting point: 76-81° C. (degradation, corrected) outgassing at 126° C.). $^1$H-NMR (400 MHz, D$_2$O) δ=9.38 (s, 1H), 9.33 (d, 1H), 9.01 (d, 1H), 8.28 (dd, 1H), 6.62 (d, 1H), 5.63 (m, 2H), 4.40 (m, 1H), 4.24 (dq, 1H), 2.23 (2×s, 6H) ppm.

Example 8. Lithium 1-((2R,3R,4S,5R)-5-(((hydrogenphosphonato)oxy)methyl)-3,4-dihydroxytetrahydrofuran-2-yl)pyridin-1-ium-3-carboxylate (I-012)

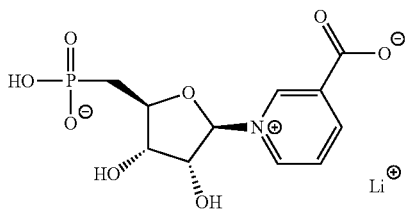 [SMILES: O=C([O-])c1ccc[n+]([C@@H]2O[C@H](CP(=O)([O-])O)[C@@H](O)[C@H]2O)c1 ; [Li+]]

A 50 mL 3 N RBF fitted with a water condenser and internal thermometer was charged with NaMN (0.100 g, 0.298 mmol, 1 eq) and 15 ml of distilled deionised water and mixed to form a solution under nitrogen. This solution was cooled using an ice/water bath (pH of solution=1.8). To this solution was then added dropwise 2.83 ml of 0.1M LiOH solution slowly via syringe so as to prevent the temperature from increasing. After this addition the pH was 4.6-4.9. The solution was then transferred into a 100 ml 1 N RBF and freeze dried overnight. This yielded a faint yellow to faint beige solid. Yield: 104.8 mg, Quantitative. Melting point: 127.5-128.3° C. (degradation-outgassing, corrected). $^1$H-NMR (400 MHz, D$_2$O) δ=9.30 (s, 1H), 9.22 (d, 1H), 8.93 (d, 1H), 8.21 (app t, 1H), 6.18 (d, 1H), 4.61 (p, 1H), 4.53 (t, 1H), 4.44 (m, 1H), 4.28 (dq, 1H), 4.14 (dq, 1H) ppm.

Example 9. Lithium 1-((2R,3R,4S,5R)-3,4-dihydroxy-5-((phosphonatooxy)methyl) tetrahydrofuran-2-yl)pyridin-1-ium-3-carboxylate (I-013)

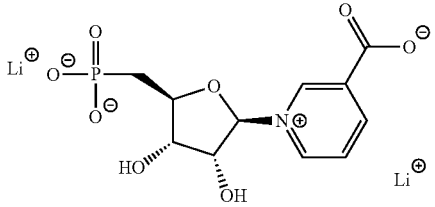 [SMILES: [Li+] ; O=C([O-])c1ccc[n+]([C@@H]2O[C@H](CP(=O)([O-])[O-])[C@@H](O)[C@H]2O)c1 ; [Li+]]

A 50 mL 3 N RBF fitted with a water condenser and internal thermometer was charged with NaMN (0.100 g, 0.298 mmol, 1 eq) and 10 ml of distilled deionised water and mixed to form a solution/faint suspension under nitrogen. This solution was cooled using an ice/water bath (pH of solution=1.8). To this solution was then added dropwise 5.82 ml of 0.1M LiOH solution slowly via syringe so as to prevent the temperature from increasing. After this addition the pH was 7-7.4. The solution was then transferred into a 100 ml 1 N RBF and freeze dried overnight. This yielded a faint yellow to faint beige solid. Yield: 102.4 mg, 99%. Melting point: 107.8-110.6° C. (degradation-outgassing, corrected). $^1$H-NMR (400 MHz, D$_2$O) δ=9.46 (d, 1H), 9.21 (s, 1H), 8.90 (d, 1H), 8.24 (app t, 1H), 6.16 (d, 1H), 4.59 (t, 1H), 4.55 (p, 1H), 4.45 (dd, 1H), 4.15 (ddd, 1H), 4.03 (ddd, 1H) ppm.

Example 10. Calcium 1-((2R,3R,4S,5R)-5-(((hydrogenphosphonato)oxy)methyl)-3,4-dihdroxytetrahydrofuran-2-yl)pyridin-1-ium-3-carboxylate (I-010)

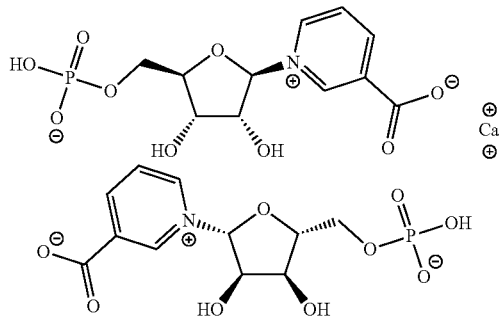

A 50 mL 3 N RBF fitted with a water condenser, rubber septum and internal thermometer, under nitrogen, was charged with NaMN (0.100 g, 0.298 mmol, 1 eq) and 15 ml of distilled deionised water and mixed to form a solution. This solution was cooled using an ice/water bath to bring the internal temperature below 5° C. To this solution was then added CaOH (10.6 mg, 0.143 mmol, 0.48 eq.). Over the next 10 minutes the stirred suspension turned to solution and left only a very faint residue of solid. The resulting solution was then freeze dried over night to give a colourless solid. Yield: 0.105 g. $^1$H-NMR (400 MHz, D$_2$O) δ=9.35 (s, 2H), 9.27 (d, 2H), 8.97 (app d, 2H), 8.24 (app t, 2H), 6.22 (d, 2H), 4.65 (p, 2H), 4.57 (t, 2H), 4.47 (m, 2H), 4.31 (dq, 2H), 4.17 (dq, 2H) ppm.

Example 11. Magnesium 1-((2R,3R,4S,5R)-5-(((hydrogenphosphonato)oxy)methyl)-3,4-dihydroxytetrahydrofuran-2-yl)pyridin-1-ium-3-carboxylate (I-011)

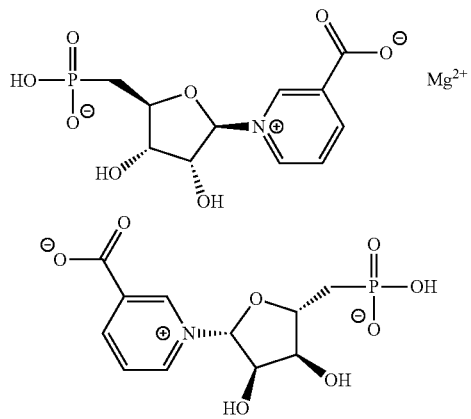

A 50 mL 3 N RBF fitted with a water condenser, rubber septum and internal thermometer, under nitrogen, was charged with NaMN (0.100 g, 0.298 mmol, 1 eq) and 15 ml of distilled deionised water and mixed to form a solution. This solution was cooled using an ice/water bath to bring the internal temperature below 5° C. To this solution was then added MgCO$_3$ (basic) (12.6 mg, 0.149 mmol, 0.50 eq.). Over the next 10 minutes the stirred suspension turned to solution and left only a very faint residue of solid. The resulting solution was then freeze dried over night to give a colourless solid. Yield: 0.111 g. $^1$H-NMR (400 MHz, D$_2$O) δ=9.55 (s, 2H), 9.30 (d, 2H), 8.96 (d, 2H), 8.28 (app t, 1H), 6.18 (d, 1H), 4.60 (m, 4H), 4.44 (m, 2H), 4.20 (m, 2H), 4.02 (m, 2H) pp Example 12. Solution Stability for Control NaMN Three separate 5 mg samples of the same batch of NaMN were completely dissolved without stirring in 0.5 ml of deuterated water (D$_2$O), each in three separate NMR tubes. All three samples were analysed at the time of dissolution via $^1$H-NMR for purity.

The first NMR tube was maintained at a temperature of 25° C. The second NMR tube was maintained at a temperature of 40° C. The third NMR tube was maintained at a temperature of 60° C. Degradation of the control NaMN was measured using $^1$H-NMR. Degradation of the control NaMN in aqueous solutions was analyzed over a period of 36 weeks (see FIG. 1). In FIG. 1, at 60° C., NaMN showed 35% degradation after a week in an aqueous solution at which point the study was halted. At 40° C., considerable signs of degradation were observed at week 2 with 15.3% of NaMN degraded when dissolved in water, at which point the study was halted. The slowest degree of degradation was observed at 25° C. with about 12.3% of NaMN degraded by week 10 as shown in FIG. 1.

Example 13: Solution Stability of the Salts of the Disclosure

The stability of the salts I-001, I-002, I-003, and I-004 in aqueous solution phase was also tested. Following the same procedure described in the control NaMN, the respective solutions of I-001, I-002, I-003, and I-004 were maintained at 25° C. and analysed for 38 weeks. As shown in FIG. 2, all salts display better stability than the controls under the same conditions of temperature and pressure. At 25° C., the degradations of the salts I-001, I-002, I-003, and I-004 remained under 2% and for at least 7 weeks. (See FIG. 2). After 24 weeks, the highest percentage of degradation of the salts observed was 4.7% for I-002. The salt I-004 maintained a low degradation of 2.6% after 34 weeks in aqueous solution. Even after 38 weeks, in solution the salt I-001 was only degraded by 4.3% (see FIG. 2)

Example 14. NAD Cell Assays

NAD levels were assayed based on the NAD cycling method of Zhu and Rand, *PLoS One* (2012), herein incorporated by reference. COV434 cells were maintained in 6 well plates and treated with the indicated compounds at a concentration of 200 uM for 4 hr. Media was removed, plates were washed in cold PBS and cells were scraped down in NAD extraction buffer containing 10 mM nicotinamide, 50 mM Tris HCl, 0.1% Triton X-100. Cells were homogenised by sonication for 5 seconds, and samples were centrifuged at 7,000 g for 5 min at 4 degrees. Aliquots were taken for later protein assay, and samples were then passed through 10 kDa amicon filters at 14,000 g, 30 min at 4 degrees to remove proteins from the sample. Each sample was measured in technical triplicate, with 25 μL sample added to 100 μL ADH cycling mix (0.2 mg/ml alcohol dehydrogenase enzyme, 2% ethanol, 100 mM Tris pH 8.5). Samples were allowed to cycle for 10 min at room temperature, followed by 50 μL addition of an MTT/PMS solution (0.1 mM phenazine methosulfate, 0.8 mM 3-(4,5-Dimethylthiazol-2-yl)-2,5-diphenyltetrazoliwn bromide), 100 mM Tris-HCl pH 8.5). Plates were then incubated for 15 min and absorbance was measured at 570 nM. NAD concentrations were extrapolated from a standard curve, and normalised to protein concentrations determined by BCA protein assay.

The results of the assay described above are shown in Table 2 (below).

TABLE 2

| Compound ID | Fold increase compared to NaMN | Fold Increase compared to NaMN on a molar basis |
|---|---|---|
| NaMN | 1.0 | 1.0 |
| I-001 | 3.0 | 3.23 |
| I-002 | 0.8 | 0.84 |
| I-003 | 1.0 | 1.08 |
| I-004 | 1.3 | 1.57 |
| I-006 | 2.3 | 2.72 |
| I-008 | 0.8 | 0.99 |
| I-009 | 1.0 | 1.39 |

From the stability tests and cellular NAD+ tests it was surprisingly and unexpectedly found that inorganic salts of NaMN are more stable under various standard and physiological conditions relative to NaMN and also unexpectedly increased the levels of NAD+ in COV434 cells, which are derived from human ovarian cells, relative to NaMN. Such results demonstrate that inorganic salts of NaMN can be useful for treating diseases and disorders related to NAD+ deficiencies.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A salt selected from the group consisting of:

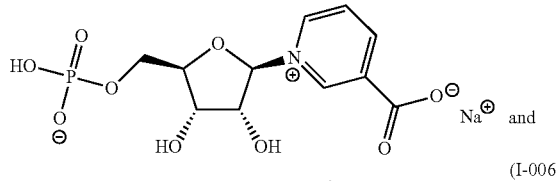

(I-001)

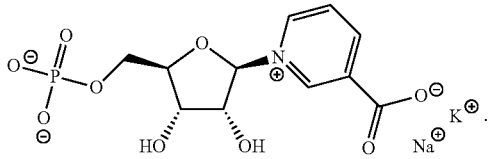

(I-006)

2. The salt of claim 1 having the structure:

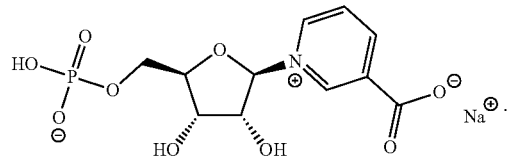 [SMILES: O=C([O-])c1ccc[n+]([C@@H]2O[C@H](COP(=O)([O-])O)[C@@H](O)[C@H]2O)c1 ; [Na+]]

3. The salt of claim 1 having the structure:

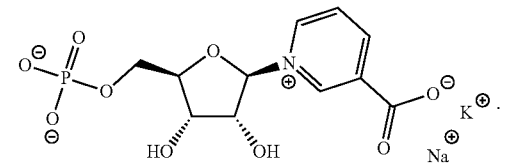 [SMILES: O=C([O-])c1ccc[n+]([C@@H]2O[C@H](COP(=O)([O-])[O-])[C@@H](O)[C@H]2O)c1 ; [K+] ; [Na+]]

4. A pharmaceutical composition comprising a salt of claim 1 and a pharmaceutically acceptable carrier.

5. A pharmaceutical composition of comprising a salt of claim 2 and a pharmaceutically acceptable carrier.

6. A pharmaceutical composition of comprising a salt of claim 3 and a pharmaceutically acceptable carrier.

* * * * *